(12) United States Patent
Glaug et al.

(10) Patent No.: US 12,263,069 B2
(45) Date of Patent: Apr. 1, 2025

(54) ABSORBENT ARTICLE WITH IMPROVED FLUID CONTAINMENT AND COMFORT

(71) Applicant: Irving Consumer Products Limited, Dieppe (CA)

(72) Inventors: Frank Glaug, Chester Springs, PA (US); James DeFelice, Rogers, AR (US); Greg Pike, Wrentham, MA (US)

(73) Assignee: Irving Consumer Products Limited, Dieppe (CA)

( * ) Notice: Subject to any disclaimer, the term of this patent is extended or adjusted under 35 U.S.C. 154(b) by 115 days.

(21) Appl. No.: 17/528,565

(22) Filed: Nov. 17, 2021

(65) Prior Publication Data
US 2022/0151841 A1    May 19, 2022

Related U.S. Application Data

(60) Provisional application No. 63/115,149, filed on Nov. 18, 2020.

(51) Int. Cl.
*A61F 13/494*    (2006.01)
*A61F 13/49*    (2006.01)
(Continued)

(52) U.S. Cl.
CPC .. *A61F 13/49017* (2013.01); *A61F 13/49466* (2013.01); *A61F 13/51121* (2013.01);
(Continued)

(58) Field of Classification Search
CPC .... A61F 13/47; A61F 13/62; A61F 13/49017; A61F 13/51121; A61F 2013/4512;
(Continued)

(56) References Cited

U.S. PATENT DOCUMENTS 3,995,637 A    12/1976  Schaar
5,064,421 A    11/1991  Tracy
(Continued)

FOREIGN PATENT DOCUMENTS

JP    O 998 891 A2  *  11/1998

OTHER PUBLICATIONS

Roe et al. United States Statutory Invention Registration. Reg. No. H1630. (Year: 1997).*

*Primary Examiner* — Catharine L Anderson
(74) *Attorney, Agent, or Firm* — SMART & BIGGAR LP

(57) ABSTRACT

The present invention relates generally to absorbent products, and, more particularly, to disposable absorbent articles that provide improvements in the containment of bodily fluid secretions. The fluid containment improvements are the result of adding one or more waist barriers to the topsheet of various absorbent articles. Adding waist barriers to the disposable absorbent articles will decrease fluid leakage at the front, back, or both waist areas of the user. In addition, the waist barrier may be made of a soft and lofty form, which will improve comfort for and reduce irritation to the user's skin. The waist barrier may improve the comfort of the user during nap time, overnight, or whenever the user is lying on their back or stomach. The waist barrier may include one or more sustainable materials.

19 Claims, 7 Drawing Sheets

(51) Int. Cl.
*A61F 13/511* (2006.01)
*A61F 13/45* (2006.01)

(52) U.S. Cl.
CPC .............. *A61F 2013/4512* (2013.01); *A61F 2013/49092* (2013.01)

(58) Field of Classification Search
CPC ...... A61F 2013/49092; A61F 13/49011; A61F 13/49466; A61F 13/4758; A61F 13/494; A61F 2013/49486; A61F 2013/49493
See application file for complete search history.

(56) References Cited

U.S. PATENT DOCUMENTS

| | | | |
|---|---|---|---|
| 5,234,422 A | 8/1993 | Sneller et al. | |
| 5,308,346 A | 5/1994 | Sneller et al. | |
| 5,460,622 A * | 10/1995 | Dragoo | A61F 13/4942 604/378 |
| 5,490,847 A | 2/1996 | Correa et al. | |
| 5,558,660 A | 9/1996 | Dreier | |
| 5,601,545 A | 2/1997 | Glaug et al. | |
| 5,797,824 A | 8/1998 | Tracy | |
| 5,827,259 A | 10/1998 | Laux et al. | |
| 6,245,051 B1 | 6/2001 | Zenker et al. | |
| 6,334,858 B1 | 1/2002 | Ronnberg et al. | |
| 6,425,889 B1 * | 7/2002 | Kitaoka | A61F 13/49466 604/385.19 |
| 6,664,440 B2 | 12/2003 | Kawamura et al. | |
| 6,881,207 B1 | 4/2005 | Tracy | |
| 9,044,358 B2 | 6/2015 | Nakajima et al. | |
| 10,524,962 B2 | 1/2020 | Raycheck et al. | |
| 10,709,618 B2 * | 7/2020 | Bishop | A61F 13/15723 |
| 2003/0050616 A1 | 3/2003 | Reynolds et al. | |
| 2006/0058767 A1 | 3/2006 | Zhang et al. | |
| 2008/0312622 A1 * | 12/2008 | Hundorf | A61F 13/5376 604/366 |
| 2012/0330260 A1 | 12/2012 | Bishop et al. | |
| 2017/0239104 A1 | 8/2017 | Jang et al. | |
| 2018/0104116 A1 | 4/2018 | Bishop et al. | |
| 2019/0358097 A1 * | 11/2019 | Chmielewski | A61F 13/5376 |
| 2021/0346210 A1 | 11/2021 | Glaug et al. | |

\* cited by examiner

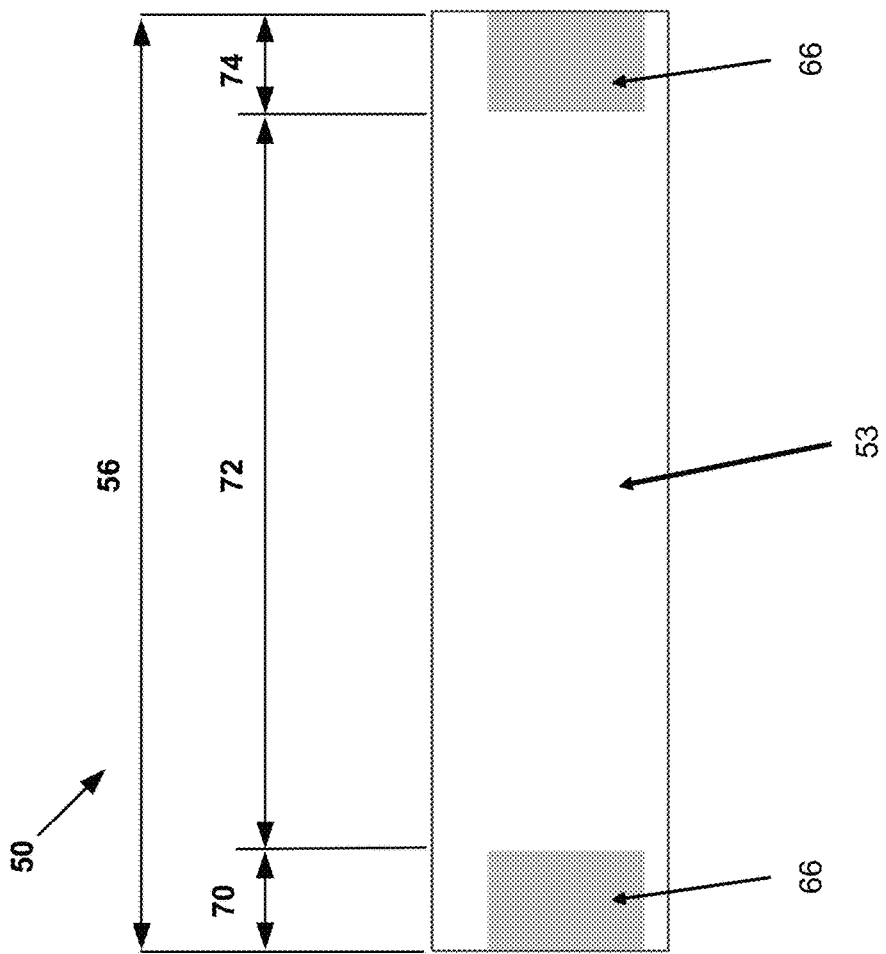
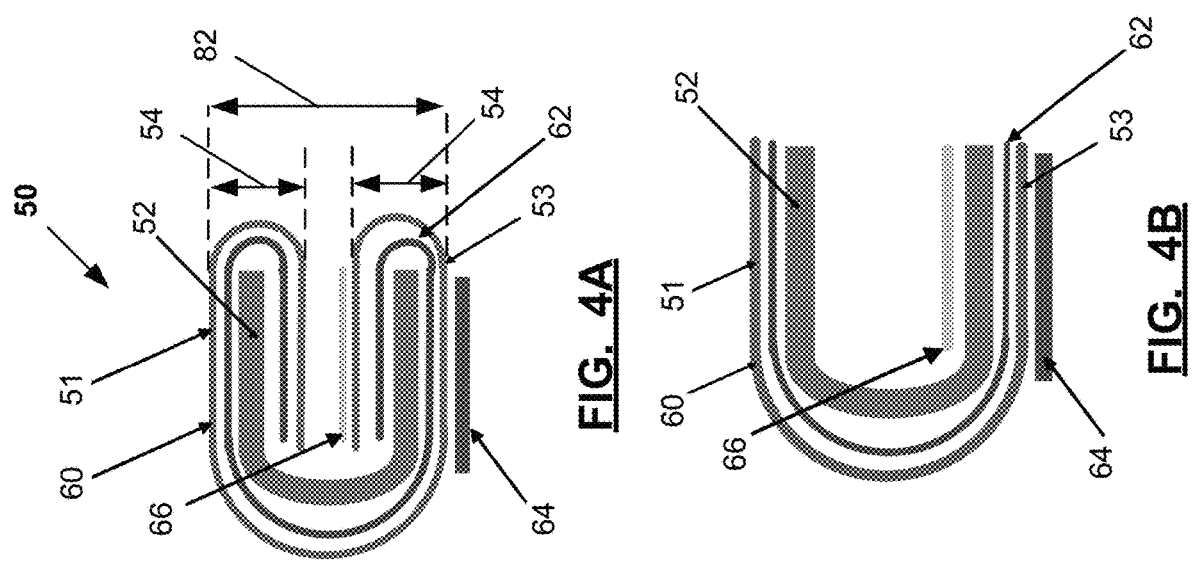
FIG. 4C
FIG. 4A
FIG. 4B

ABSORBENT ARTICLE WITH IMPROVED FLUID CONTAINMENT AND COMFORT

CROSS-REFERENCE TO RELATED APPLICATIONS

This application claims the benefit of U.S. Provisional Application No. 63/115,149 filed on Nov. 18, 2020, which is incorporated by reference herein in its entirety.

FIELD

The described embodiments relate generally to disposable absorbent articles, and, more particularly, to a disposable undergarments and pants (adult and child), diapers and briefs (adult and child), belted garments, incontinence pads, male guards, feminine care pads, wound care dressings and the like.

BACKGROUND

The following is not an admission that anything discussed below is part of the prior art or part of the common general knowledge of a person skilled in the art.

There are several types of commercially available products for the absorption of bodily fluids. Such absorbent products are available in different types, designs, and dimensions, each one having one or more unique features. For example, training pants, baby diapers, adult diapers, adult pants, and incontinence guards are products designed for the containment of urine and excrement. There are other types of disposable absorbent articles, such as feminine hygiene products (e.g., heavy and light incontinence pads, panty liners, etc.) that are designed to contain and absorb urine and/or menses by female wearers.

Absorbent products typically include a topsheet facing the body of the wearer, a backsheet facing the garment of the wearer and an absorbent core located between the topsheet and backsheet. In some cases, Acquisition Distribution Layers (ADL) are provided between the topsheet and the absorbent core. ADLs help in the fast absorption and distribution of bodily fluids. In addition, standing leg cuffs may be provided at each side of the absorbent core, in the longitudinal direction of the product, to help prevent side leakage of the bodily fluids within the crotch and leg regions of the body. The leg and waist openings of the product are gathered with elastomeric material(s) to help support the product against the skin of the user and reduce leakage of the bodily fluids at the waist and legs.

While these types of absorbent articles may collect body fluid discharge as intended, many of these products tend to leak when exposed to higher fluid volumes, longer periods of wear, and increased stress conditions when the user is active. This leakage may lead to frequent changing of the user's outer garments, bed sheets, baby seat covers, etc. In addition to the nuisance of cleaning-up and washing clothes, there is always the embarrassment to both the user and caretaker of soiled clothing and surroundings.

Current commercially available absorbent products are generally insufficient in providing an effective fluid barrier that substantially prevents fluid leakage, especially when the product is relatively saturated with fluid and is worn for long periods, such as overnight use. Some commercial absorbent products provide Standing Leg Cuffs for leakage protection in the crotch and leg areas. However, Standing Leg Cuffs do not provide leakage protection in the front and back waist areas of the product, especially when the user is sleeping on either their back or on their stomach. There are current commercially available absorbent products that contain waist barriers, containment pouches, or waistbands that help reduce leakage at the either front or back end of the product or both. Unfortunately, these executions offer limited leakage protection at the front or back waist areas of the product when the absorbent core becomes relatively saturated and/or if there is a gap between the product and user's skin.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with one aspect of this disclosure, which may be used alone or in combination with any other aspect, there is provided an absorbent article having a front edge, a back edge, two longitudinally extending side edges, a front waist region, a rear waist region, a crotch region extending between the front waist region and the rear waist region, a skin-facing side, and a clothing-facing side, the absorbent article comprising:

a topsheet, the topsheet being liquid pervious;
a backsheet coupled to the topsheet, the backsheet being liquid impervious;
an absorbent core disposed between the topsheet and backsheet, the absorbent core containing at least one absorbent material;
an acquisition distribution layer disposed between a bottom side of the topsheet and a top side of the absorbent core;
first and second standing leg cuffs, each standing leg cuff includes:
a base coupled to the topsheet; and
one or more elastics coupled to a top of the standing leg cuff; and
a waist barrier located on the skin-facing side of one of the front waist region or the rear waist region, the waist barrier including a resilient member forming a cavity, the resilient member being inherently biased such that the resilient member is compressible towards the skin-facing side to form a biasing force in a direction away from the skin-facing side.

In any embodiment, the absorbent article may further comprise a height between the topsheet and a top portion of the waist barrier on a cavity-facing side of the waist barrier, the waist barrier may have an uncompressed state with a first height and a compressed state when worn by a user with a second height, wherein the first height may be greater than the second height.

In any embodiment, the first height may be at least twice a thickness of the waist barrier.

In any embodiment, the resilient member may be at least partially covered by a cover sheet.

In any embodiment, the cover sheet may be a hydrophobic nonwoven.

In any embodiment, the waist barrier may be at least partially absorbent.

In any embodiment, at least a portion of the waist barrier may comprise one or more of bamboo, rayon, viscose, or cotton.

In any embodiment, the waist barrier has a length in a direction transverse to the longitudinal side edges that may be at least a width of the crotch region.

In any embodiment, the waist barrier may have at least one fold defining a top portion and a bottom portion with the cavity located between the top portion and the bottom portion.

In any embodiment, the waist barrier may be folded prior to being attached to the absorbent article.

In any embodiment, the waist barrier may further comprise first and second longitudinal end regions and a middle region therebetween, the first and second longitudinal end regions of the top portion and the bottom portion may be bonded together such that an unbonded middle region forms the cavity between the top portion and the bottom portion.

In any embodiment, an underside of the bottom portion may be bonded to the topsheet such that the middle region of the top portion extends away from the bottom portion due to the bias of the resilient member.

In any embodiment, the waist barrier may further comprise:
- a longitudinal edge proximate one of the front edge or the rear edge;
- a first longitudinal end region;
- a second longitudinal end region; and
- a middle region between the first and second longitudinal edge regions, the longitudinal edge, first longitudinal end region, and second longitudinal end region being bonded to the topsheet such that an unbonded middle region forms the cavity between the waist barrier and the topsheet due to the bias of the resilient member.

In any embodiment, the absorbent article may further comprise a second waist barrier, wherein the waist barrier is a first waist barrier.

In any embodiment, the first waist barrier may be located in the front waist region and the second waist barrier may be located in the rear waist region.

In any embodiment, the waist barrier may be attached to the absorbent article under tension.

In any embodiment, the waist barrier may be attached to the absorbent article in a latent state.

In any embodiment, the topsheet and waist barriers may comprise different materials.

In any embodiment, at least one of the materials of the waist barrier may comprise a form.

In any embodiment, at least one of the materials of the waist barrier may comprise a material capable of containing fluid, such as a non-woven. Optionally, the nonwoven may also be sustainable, for example, the nonwoven material may be made at least partially from recycled materials.

In any embodiment, at least one of the materials of the waist barrier may comprise a hydrophobic nonwoven.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 4A shows a cross-sectional view of the disposable absorbent article of FIG. 1, along the line B-B in FIG. 1;

FIG. 4B shows a cross-sectional view of the disposable absorbent article of FIG. 1 in accordance with another example embodiment, along the line B-B in FIG. 1;

FIG. 4C shows a top view of the waist barrier in the rear waist area of the absorbent article of FIG. 1, along the line C-C in FIG. 1;

Figure 1:
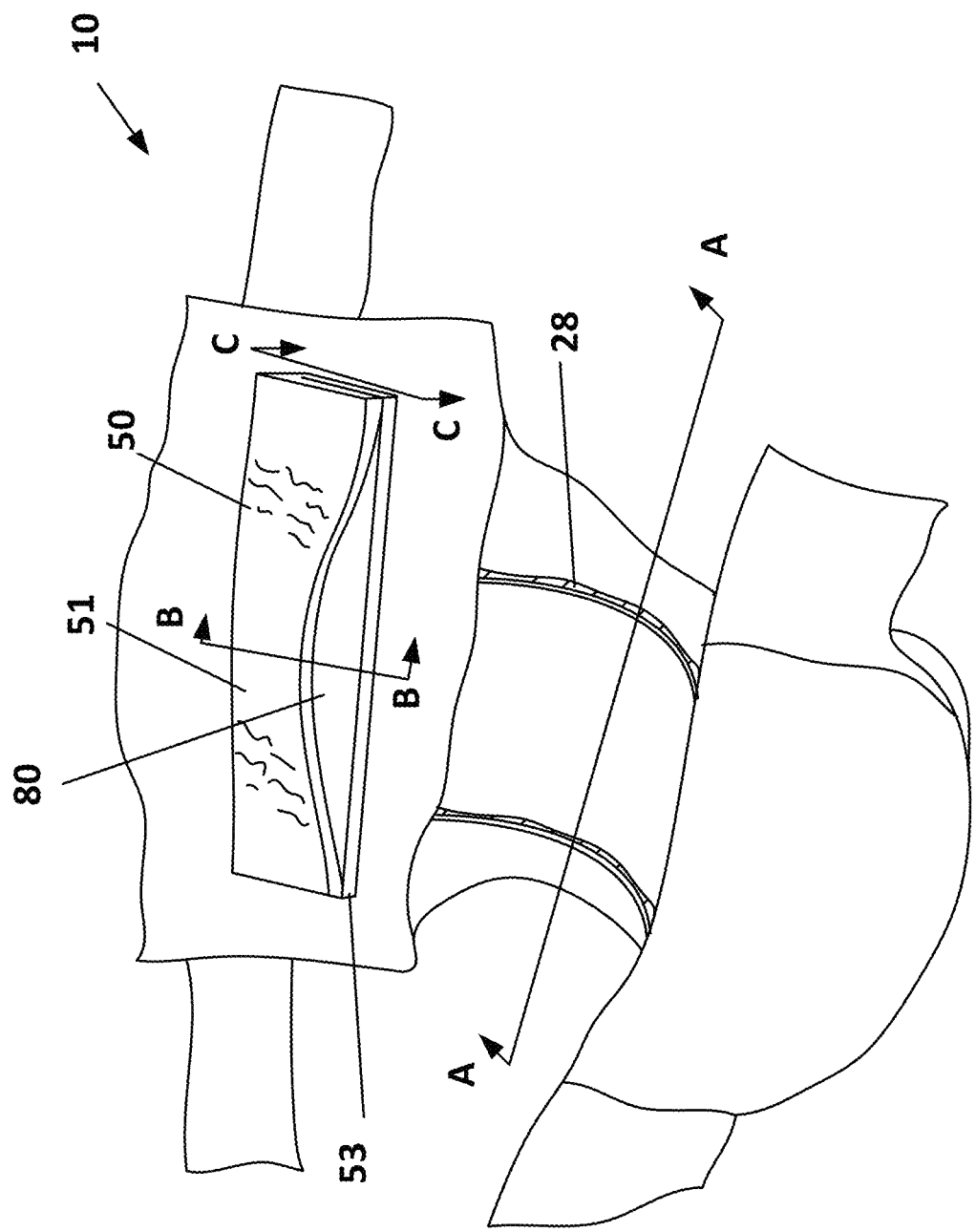
FIG. 1 shows a perspective view of a disposable absorbent article having a waist barrier located at a rear waist area, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

As used herein and in the claims, two or more parts are said to be "coupled", "connected", "attached", or "fastened" (which may all be used interchangeably) where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. None of the terms "coupled", "connected", "attached", and "fastened" distinguish the manner in which two or more parts are joined together. For example, two or more parts may be "coupled", "connected", "attached" or "fastened" by bonding them together with an ultrasonic or heat bond or other technique that does not require a bonding agent, with a bonding agent such as an adhesive, through mechanical bonding, with a mechanical fastener, or in any other manner.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Disposable absorbent articles, such as disposable undergarments, pants, diapers, other garments, have either a closed (e.g., pants) or open (e.g., diapers) product chassis, with an absorbent core system located between two substrate layers. The first substrate layer is on the inside of the article, often referred to as a topsheet, and the second substrate is on the outside of the article, often referred to as a backsheet. The absorbent core system often contains a mixture of pulp and super absorbent polymer (SAP). In some cases, absorbent cores have been designed to be thinner to improve the comfort of users and to provide a better product fit. One process of making the absorbent core thinner is to increase the quantity of SAP and decrease the quantity of pulp. However, SAP requires a certain amount of void volume to properly absorb liquids. Increasing the SAP relative to the pulp may result in fluid that is not absorbed rapidly, often referred to as free fluid. Accordingly, an acquisition distribution layer (ADL) may be added on top of the absorbent core. The ADL can provide the void volume needed to absorb the free fluid the SAP inside the absorbent core could not rapidly absorb. In addition to the ADL, a standing leg cuff is provided along each longitudinal side of the absorbent core, thereby reducing fluid leakage along the crotch and leg areas. In various embodiments, the standing leg cuffs may be positioned above the absorbent core or transversely outboard of the absorbent core.

Referring to FIGS. 1-4 and 6-7, shown therein is an example embodiment of a disposable absorbent article 10. The article 10 has a topsheet 12 and a backsheet 14. In this example embodiment, the backsheet 14 is formed of two layers: a poly barrier 16 and a nonwoven backsheet 18. An absorbent core 20 is disposed between the topsheet 12 and the backsheet 14. An acquisition distribution layer 22 is positioned between the topsheet 12 and the absorbent core 20. In this example embodiment, the absorbent core 20 is positioned between a top core wrap 24 and a bottom core wrap 26. Either or both of the top and bottom core wraps 24, 26 may be a tissue or a nonwoven web. The top and bottom core wraps may fully or partially cover, surround, or wrap around all or part of the absorbent core 20.

Figure 2:
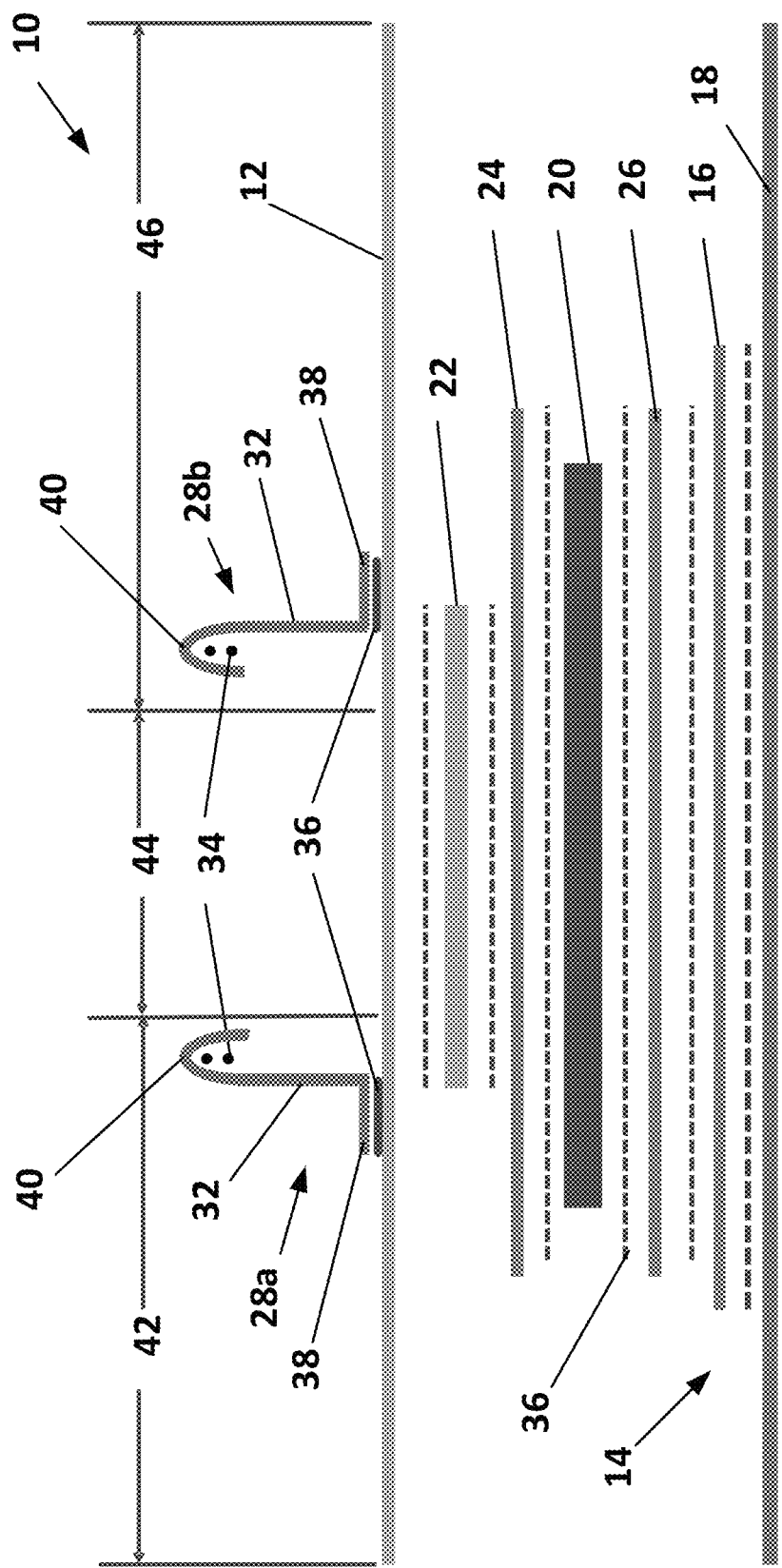
FIG. 2 shows a cross-sectional view of the absorbent article of FIG. 1 along the line A-A in FIG. 1.

In the example of FIGS. 1-2, the article 10 includes a first standing leg cuff 28a and a second standing leg cuff 28b, referred to together as standing leg cuffs 28. The standing leg cuffs 28 include a cuff web 32 and one or more elastic strands 34. In some embodiments, the standing leg cuffs may include a plurality of elastic strands 34. As exemplified, the standing leg cuffs are coupled to the topsheet 12 by one or more bonds 36. It will be appreciated that the bond 36 may be any bond type capable of securing various components of the article 10 to another component of the article 10. For example, as illustrated, the bonds 36 are adhesive. In some embodiments, the bonds 36 may be ultrasonic bonds. In some embodiments, some of the bonds 36 may be adhesive and some may be ultrasonic.

It will be appreciated that the various layers of the article 10 may be formed of different materials. The topsheet 12 is at least partially liquid pervious. For example, the topsheet 12 may be a hydrophilic nonwoven web. The ADL 22 may be made of a high loft carded nonwoven. In some embodiments, the ADL 22 may include or be formed of an apertured poly film. The apertures of the apertured poly film may be 3-dimensional. The absorbent core 20 may be formed of a single layer or a dual layer. In some embodiments, the absorbent core 20 may be made of an airlaid material. The absorbent core 20 has one or more absorbent materials.

In some embodiments, the absorbent core 20 may have a plurality of absorbent materials. It will be appreciated that the absorbent core 20 may be made of pulp, SAP, or a blend of pulp and SAP. In FIGS. 1-2, the absorbent core 20 includes a single layer containing a blend of pulp and SAP. It will be appreciated that the absorbent material in the absorbent core may be a single pulp material or a plurality of pulp materials. For example, the absorbent material may include one or more of the following: rayon fibers, cotton fibers, bamboo fibers, soft pine, eucalyptus fibers, superabsorbent polymer particles, superabsorbent polymer fibers, peat moss, cross-linked cellulose fibers, cellulose acetate, polypropylene tow, polymer fibers, surfactant treated nonwovens, binder fibers, linen fibers, hemp fibers, ramie fibers, jute fibers, miscanthus pulp fibers, natural cellulose fibers, sponges, absorbent forms, etc.

As described above, the backsheet 14 may be a laminate that includes both the poly barrier 16 and the nonwoven backsheet 18. The poly barrier 16 is typically fluid impervious. In some embodiments, the poly barrier 16 may be a poly film. In some embodiments, the poly barrier 16 may be a breathable poly material, such as a microporous film. It will be appreciated that the backsheet 14 and/or the absorbent core 20 may include a poly laminate whereby the poly film is extruded onto the nonwoven web.

In some embodiments, at least a portion of the topsheet 12 may be treated with a surfactant. The surfactant renders the topsheet 12 hydrophilic, thereby facilitating fluid flow to areas that have been surfactant treated. For example, referring still to FIGS. 1-2, the topsheet 12 has three zones: a left zone 42, a middle zone 44, and a right zone 46. In some embodiments, the middle zone 44 may be treated with the surfactant, such that the middle zone 44 has increased hydrophilicity relative to the left and right zones 42, 46. In some embodiments, the topsheet 12 may be hydrophobic. Accordingly, the topsheet 12 may be strategically treated by the surfactant to improve the fluid flow from the topsheet 12 to the ADL 22. In some embodiments, the middle zone 44 may be processed to allow fluids to flow through. For example, the portion of the topsheet 12 in the middle zone 44 may be perforated or formed of a porous material to allow fluid to flow more easily through the topsheet 12.

As exemplified in FIGS. 1-2, the base 38 of each standing leg cuff 28 is coupled to the topsheet 12 within the left zone 42 and right zone 46 through a bond 36. In some embodiments, the standing leg cuffs 28 may be coupled to the topsheet 12 adjacent the transverse inboard edges of the left and right zones 42, 46. By coupling the base 38 of the standing leg cuffs 28 along these edges, the risk of fluid wicking underneath the standing leg cuffs 28 is decreased. To achieve the standing function of each standing leg cuff 28, one or more elastics 34 are tensioned or elongated and coupled to the cuff web 32 at its top end 40. The cuff web 32 is then folded over and coupled to itself to cover the elastics 34. The cuff web 32 may be closed over the elastics 34 by any means known in the art, such as with an adhesive, mechanical fastening or by ultrasonic bonding. By folding the cuff web 32 over the elongated elastics 34, the standing leg cuff 28 is lifted away from the topsheet and may extend upwardly from the topsheet 12, thereby allowing the standing leg cuffs 28 to come into contact with the body of a user when in use. The cuff web 32 comprises of hydrophobic nonwoven with a certain amount of hydro-head. For example, in some embodiments, the water column (per EDANA WSP 80.6 Test Method) ranges from 12-15 mbar.

Waist Barrier

One of the most important functions of disposable absorbent articles is to contain bodily fluids quickly and adequately, in order to prevent fluid leakage outside of the product. In some cases, the absorbent cores may be overwhelmed in certain regions with the high volumes of fluid that is emitted upon them in a short period of time. As described above, some absorbent core designs have been thinned by increasing the ratio of SAP to pulp in the composition of the absorbent core. SAP takes longer to absorb liquid than pulp, thereby occasionally resulting in free fluid that is not absorbed immediately by the absorbent core. In addition, the absorbent core, or a portion of it, can become saturated with fluid, which slows down the flow of fluid into the core. The possibility of free fluid flowing within the product and the inability of the absorbent core to absorb all fluid at once results in a need for an improved fluid barrier and containment system.

In addition to thinner absorbent core designs, there is also a gravitational effect on the fluid. Testing baby diapers and training pants on baby mannequins have demonstrated that commercial products are limited in leakage protection at the front and back waist areas, especially when the absorbent core becomes saturated. For instance, when the user is laying on either their belly or back, the fluid flows down the absorbent core 20 to the lowest point in the absorbent article 10. The lowest point can be either in the front section of the absorbent article 10, when laying on their belly, or in the rear section of the absorbent article 10, when laying on their back. The fluid can flow down to these sections and over saturate the absorbent core 20. Saturation of the absorbent core happens especially when the user is laying on their back or stomach for long periods of time, such as overnight. Urine may gush down to the back or front end of the product, due to gravity and the position of the user, similar to a waterfall. The standing leg cuffs 28 helps prevent the fluid from overflowing the sides of the absorbent article 10, within the crotch area, and longitudinally directs it towards the front or back section. When the absorbent core 20 is saturated at the front or back section, the fluid can easily leak out at either the front waist or back waist of the absorbent article 10.

Typical previously known waist barriers, containment pouches and elastic waistbands offer limited protection to prevent the urine from flowing out of the product, thereby causing leakage. They are flattened out by both the weight of the user and the tension applied to the user when the article is worn. As the absorbent core gets saturated, the superabsorbent polymer swells and the urine eventually flows along the top surface. The swelling effect of the core allows it to rise above the commercial waist barrier executions and the urine simply flows over the top and leaks out the product. Additionally, the tightness of the waistband against the skin, can cause red marking. Red markings may occur because absorbent products are usually applied taut to the body to reduce drooping and the tension at the waist may be increased when the user moves from standing to sitting positions.

Another deficiency with typical previously known waist barriers is that they do not retain any urine. There are many instances where urine flows outside of the absorbent core and becomes "free fluid". This "free fluid" can leak out of the product when pressure is applied to the product or when the user moves. A fluid-containing (e.g., absorbent or adsorbent) leakage barrier may prevent fluid from leaking out of the product, while also retaining fluid over time.

Accordingly, a more efficient waist barrier may improve leakage protection, primarily during overnight use, along the front and/or back waist areas of the product. For example, referring to FIGS. 1-7, shown therein are exemplary embodiments of an absorbent article 10 with improved leakage protection and comfort. The article 10 includes one or more waist barriers 50. The waist barrier 50 may be lofty, may be able to at least partially absorb and/or adsorb fluid, and may act like a spring to close-up any open gaps between the article 10 and the skin of the user. The waist barrier may be soft and cushiony to reduce skin irritation and improve skin wellness of the user. For example, absorbent articles 10 may exert higher pressure along the waist area, since it is applied under tension to keep the product from drooping or sagging on the user. Pressure along the waist area may also increase when the user is in the sitting position and their stomach expands. Absorbent articles 10 are usually placed on the user in the standing or laying-down position, when the stomach area is flatter. A softer and more cushioned material in the waist area will help improve comfort, as well as reduce red marking and skin irritation, due to the applied pressures to the skin.

It will be appreciated that, while the waist barrier 50 may be used in any absorbent article, the waist barrier 50 may have improved usage during overnight, nap time, or whenever the user is in a primarily horizontal position. Many babies are generally in a horizontal position until they reach Diaper size 3. Bedridden patients are also mostly situated in the horizontal position.

Structure of the Waist Barrier

As exemplified in FIGS. 4A and 4B, the waist barrier 50 includes a resilient material 52. As exemplified in FIG. 1, the resilient member 52 is in a neutral state after it has been applied to the absorbent article 10. The resilient member 52 has an inherent bias such that the resilient member is compressible towards the topsheet 12 to form a biasing force in a direction away from the topsheet 12. Accordingly, the resilient member 52 acts with a spring force to bias the waist barrier 50 towards the user, when worn.

In other words, the waist barrier 50 has an uncompressed state when not worn by a user and a compressed state when worn by the user. When the waist barrier 50 is in the compressed state, gaps between the article 10 and the skin of the user may be filled by the waist barrier 50. For example, when the user wears the article 10, the resilient member 52 biases the waist barrier 50 upwards towards the skin of the user. The bias of the resilient member 52 allows the waist barrier 50 to fill gaps between the article 10 and the skin of the user.

In some embodiments, the resilient member 52 may be deformable to contour to the shape of the user. For example, when the user moves from a standing position to a sitting position, the stomach of the user typically presses on the waist of the absorbent article. The increased pressure on the waist barrier 50 may cause the resilient member 52 to compress. The bias of the resilient member 52 allows the waist barrier 50 to compress without causing discomfort to the user, while maintaining the seal against the skin of the user. Additionally, the bias of the resilient member 52 may prevent new gaps between the article 10 and the skin of the user despite change in pressure against the waist barrier 50. Accordingly, an improved leakage barrier is created.

In some embodiments, the resilient material 52 may be a form. The resilient member 52 may be a soft and lofty material. In some embodiments, the resilient member thickness may be 2 mm. It will be appreciated that the resilient member thickness may range, for example, including but not limited to, 1-20 mm.

In some embodiments, the resilient material 52 may be a material capable of containing a fluid. A material that is fluid-containing means that the material can hold or contain a fluid. For example, in some embodiments, the material may be able to contain a certain amount of fluid, ranging from 5 g/g to 25 g/g. In other words, when rated at 5 g/g for example, for every gram of material, the fluid-containing material can contain 5 grams of fluid under atmospheric pressure. For example, in some embodiments, the resilient material 52 may be a lofty nonwoven. The lofty nonwoven may include, but is not limited to, bamboo, rayon, viscose, polypropylene, or any combination thereof. In some embodiments, the resilient material 52 may be a form.

In some embodiments, the fibers in the resilient material 52 may be sustainable. For example, the resilient material 52 may include, but is not limited to, viscose, bamboo, rayon, cotton, or any combination thereof. In some embodiments, the material of the resilient member may be 40 gsm in basis weight. It will be appreciated that the material of the resilient member may range, for example, including but not limited to, 10-200 gsm.

In some embodiments, the resilient member 52 may be at least partially covered by a cover sheet 60. As exemplified in FIGS. 4A and 4B, the cover sheet 60 is a layer of nonwoven 60. It will be appreciated that the cover sheet 60 may be bonded by any means to the resilient member 52. As illustrated, a continuous laminating adhesive 62 may be used to adhere the nonwoven 60 to the resilient member 52.

During use, the nonwoven 60 contacts the skin of the user. The nonwoven 60 may improve the comfort of the user by providing a soft cover for the resilient member 52. For example, in some embodiments, the resilient member 52 may be formed of a form with a high coefficient of friction along its surface. The addition of the cover sheet 60 may reduce the coefficient of friction of the resilient member 52. Accordingly, the combination of the reduced coefficient of friction of the cover sheet 60 and the compressibility of the resilient member 52 may improve the comfort of the user. In some embodiments, the basis weight of the nonwoven 60 may be 12 gsm. It will be appreciated that the nonwoven basis weight may range, for example, including but not limited to, 7-60 gsm.

In some embodiments, the cover sheet 60 may be formed of a liquid impermeable layer. For example, the cover sheet 60 may be a poly film or treated nonwoven. The liquid impermeable cover sheet 60 may reduce leakage through the waist barrier 50. In some embodiments, the cover sheet 60 may be formed of a laminate. For example, the cover sheet 60 may have a first layer that is liquid impermeable, such as a poly film, and a second layer that is formed of a softer material, such as a nonwoven. The poly film layer of the cover sheet 60 may reduce leakage through the waist barrier 50, while the nonwoven layer of the cover sheet 60 may improve the comfort of the waist barrier 50 against the skin of the user.

The waist barrier 50 may be folded to create the spring-like bias in the resilient member 52. For example, as exemplified in FIG. 4A, the waist barrier 50 is folded in a "c" configuration, to form a top portion 51 and a bottom portion 53. The folded waist barrier 50 may then be applied to the absorbent article 10. To secure the waist barrier 50 to the article 10, a bond 64 may be used along the non-skin facing side of the bottom portion 53 of the waist barrier 50. As exemplified, the bond 64 may be continuous across the length of the waist barrier 50. It will be appreciated that the cover sheet 60 may cover any portion of the resilient member 52. For example, the cover sheet 60 may cover at least some of the top portion 51 of the resilient member 52. In some embodiments, the cover sheet 60 may extend to the interior of the "c" configuration, as exemplified in FIG. 4A, or may cover the exterior of the waist barrier 50, as exemplified in FIG. 4B.

To create the bias of the resilient member 52, an intermittent bond 66 may be used to secure the top portion 51 to the bottom portion 53. As exemplified in FIG. 4C, the waist barrier 50 has a first longitudinal end region 70, a middle region 72, and a second longitudinal end region 74. As exemplified in FIGS. 4A to 4C, each longitudinal end region 70, 74 of the top portion 51 is secured to the bottom portion 53 with the intermittent bond 66. Accordingly, with each longitudinal end region 70, 74 bonded to the article 10, the middle region 72 of the top portion 51 remains unsecured to the bottom portion 53. Due to the nature of the resilient member 52, by folding the waist barrier 50 into a "c" configuration, the top portion 51 of the waist barrier 50 is biased away from the bottom portion 53. Thus, the bottom portion 53 is secured to the article 10, while the middle region 72 of the top portion 51 is free to extend outwardly from the article 10, forming a leakage barrier in the waist region.

It will be appreciated that the bonds 62, 64, 66 may be any bond type capable of securing various components of the article 10 to another component of the article 10. For example, as illustrated, the bonds 62, 64, 66 are adhesive. In some embodiments, the bonds may be ultrasonic bonds. In some embodiments, some of the bonds may be adhesive and some may be ultrasonic.

As exemplified in FIGS. 1, 3, 4, and 6-7, the outwardly extending middle region 72 forms a cavity 80 between the bottom portion 53 and the top portion 51. The cavity 80 may be used to provide an improved leakage barrier for the article 10. For example, the cavity 80 may provide additional storage for urine and fecal leakage, while also creating a barrier.

Figure 3:
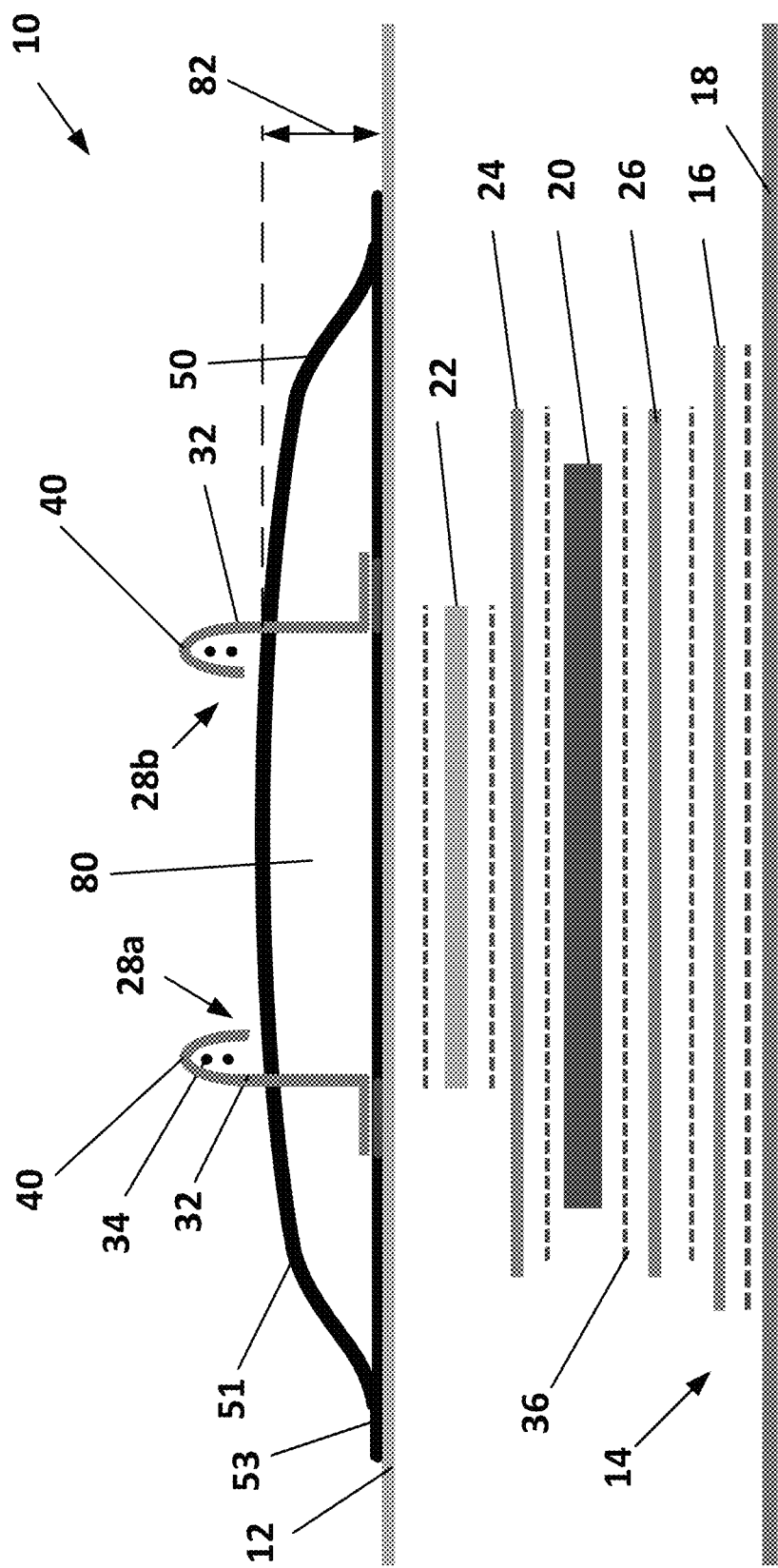
FIG. 3 shows a cross-sectional view of the absorbent article of FIG. 1 along the line A-A in FIG. 1, with the disposable article in a stretched state.

It will be appreciated that the size of the cavity 80 may vary depending on the user. As illustrated in FIG. 3, the waist barrier 50 has a height 82 between the topsheet 12 and the top portion 51 on a cavity-facing side of the waist barrier 50. When the waist barrier 50 is in the uncompressed state (i.e., not worn by a user), the height 82 may be greater than the height 82 of the waist barrier 50 in the compressed state (i.e., worn by a user). Depending on the size of the article 10 and the pressure exerted by the user when wearing the article 10, the height 82 may vary. In some embodiments, the height 82 in the uncompressed state may be at least twice a thickness 54 of the waist barrier 50.

In some embodiments, the waist barrier 50 may be continuously bonded to the article 10 along a longitudinal edge (not shown). Accordingly, the topsheet 12 may be used as the bottom portion 53 of the waist barrier 50, thereby forming the cavity 80 between the topsheet 12 and the waist barrier 50.

In some embodiments, the softened contact between the waist barrier 50 and the skin of the user may allow the waist barrier 50 to be stretched and then applied to the absorbent article 10 under tension. Accordingly, the waist barrier 50 may also act as a waistband to improve the fit of the absorbent article 10 on the user. The material of the resilient member 52 may act as a buffer to protect the skin from any tension applied to the body by the absorbent article 10. Accordingly, when, for example, form is used for the resilient member 52, a higher quantity of soft form material may reduce the likelihood of skin irritation. The loftiness and softness of the waist barrier 50 may provide a more cushioned and smoother material in direct contact with the body, thereby improving the comfort and skin wellness of the user. The combination of a softer material a particular tension may therefore provide for reduced leakage without compromising the comfort of the user.

It will be appreciated that the waist barrier 50 may be absorbent, adsorbent, or both absorbent and adsorbent. In other words, as described above, the waist barrier 50 may include a material capable of containing fluid. To achieve an absorbent and/or adsorbent waist barrier 50, in some embodiments, the interior of the waist barrier 50 may be at least partially hydrophilic, while the outside of the waist barrier 50 may be hydrophobic. For example, the resilient member 52 may be hydrophilic and the cover sheet 60 may hydrophobic. Accordingly, the resilient member may contain, absorb, and/or adsorb liquid into the waist barrier 50, while the hydrophobic cover sheet 60 may reduce leakage through the waist barrier 50. In other words, the resilient member 52 may be hydrophilic and the nonwoven 60 may be hydrophobic with a certain amount of hydro-head. For example, in some embodiments, the water column (per EDANA WSP 80.6 Test Method) ranges from 12-15 mbar.

In some embodiments, one or more materials forming the waist barrier 50 may be treated with a surfactant to increase the fluid-containing capability of the waist barrier 50. For example, the interior of the waist barrier 50, such as the interior surface of the resilient member 52, may be treated with a surfactant. For example, a high-loft nonwoven, known as an Acquisition Distribution Layer, may act as the resilient member 52, and may be treated with a surfactant.

In some embodiments, the resilient member 52 may include a material that has fluid-containing and sustainable fibers. Sustainable materials capable of containing fluid may provide a dual benefit to consumers concerned with the use of environmentally friendly materials, by providing both improved leakage protection and the use of sustainable materials.

In some embodiments, resilient member 52 may be hydrophobic. The resilient member 52 may also be at least partially absorbent over time. For example, when a soft form 52 is used, the soft form 52 may contain small holes in the structure that are hydrophobic. However, pressure over prolonged time may allow fluid to pass into the holes. In other words, the hydrophobic form 52 acts first as a barrier against fluid leakage. Then, if there is free fluid in contact with the form 52, it may absorb the free fluid and keep it from leaking out of the absorbent article 10. For example, in embodiments without the cover sheet 60, the resilient member 52 may be hydrophobic to reduce leakage through the waist barrier 50.

In some embodiments, the waist barrier 50 can be applied in the back waist section of the absorbent article 10. This location may improve leakage protection, thereby preventing urine and fecal leakage during nap or overnight use, especially for girls or women, when they are laying on their back for a prolonged period. In addition, this location may be ideal for babies who fit in Diaper sizes of Newborn to 3. Babies lay mostly on their back position during these stages.

In some embodiments, the waist barrier 50 can be applied in the front waist section of the absorbent article 10. This location may improve leakage protection, thereby preventing urine and fecal leakage during nap or overnight use, especially for boys or men, when they are laying on their belly for a prolonged period.

In some embodiments, the waist barrier 50 may be applied to both the front and back waist sections of the absorbent article 10. These locations may improve leakage protection, thereby preventing urine and fecal leakage during nap or overnight use, especially for unisex use, when users are laying on their back or bellies over a prolonged period. The waist barrier 50 could be customized for gender specific products. For instance, fluid leakage is more probable at the front end of the absorbent article 10 for males, who often lay on their bellies. "T" shaped absorbent cores were specifically designed for boys in baby diapers, mainly for this reason. In contrast, fluid leakage is more probable at the back end of the absorbent article 10 for females, who lay on their backs. In terms of a unisex products, waist barriers 50 can be placed at both the front and back ends of the absorbent article 10 to reduce leakage.

In some embodiments, the waist barrier 50 may have a length 56 that is longer than the width of the crotch region of the absorbent article 10, as exemplified in FIGS. 1 and 3. It will be appreciated that a length 56 of the waist barrier 50 may vary depending on the desired use. For example, the length 56 of the waist barrier 50 may be less than, equal to, or greater than the width of the crotch region. In some embodiments, the waist barrier 50 may extend across the entire width of the front and/or rear waist regions. As exemplified in FIGS. 6 and 7, the length 56 of the waist barrier 50 is approximately the same as the width of the crotch region of the absorbent article 10.

Accordingly, the waist barrier 50 may improve leakage protection, absorption of free fluid, comfort, skin irritation and allow for gender specific options.

In some embodiments, as exemplified in FIGS. 1-3 and 6-7, the absorbent article 10 may include both standing leg cuffs 28, for the prevention of fluid leakage at the sides, and the waist barrier 50, for the prevention of fluid leakage at one or both ends of the product. Using both standing leg cuffs 28 and the waist barrier 50 results in an increased perimeter of leakage protection around the absorbent core 20. It will be appreciated that the standing leg cuffs 28 and the waist barrier 50 may surround either a portion or the entirety of the perimeter around the absorbent core 20. Reducing fluid leakage around the entire perimeter of the absorbent core 20 may provide improved absorbency performance during use for both day and night.

It will be appreciated that the improved fluid containment and comfort features described above may be used in a variety of different absorbent products, such as, for example, training pants, baby diapers, adult diapers, adult pants, youth pants, incontinence pads, incontinence male guards, wound care, feminine hygiene articles, etc.

For example, referring to FIGS. 1-3 and 6-7, shown therein is an exemplary embodiment of an absorbent article 10 that is a diaper. As described above, the waist barrier 50 can be attached to the inside of the absorbent article 10 at either the front waist area, back waist area, or both, in order to improve the leakage and comfort of the diaper 10.

Manufacturing an Absorbent Article with a Waist Barrier

Referring to FIGS. 4A and 4B, shown therein are exemplary embodiments of the waist barrier 50 by itself, before being attached to an absorbent article 10. The fold adhesive 66 may be applied, in an intermittent pattern, to the waist barrier 50 before attachment to the absorbent article 10. The intermittent pattern 66 may allow the waist barrier 50 to spring-open in the middle region 72, thereby filling open gaps between the absorbent article 10 and the skin of the user and reducing leakage. After the fold adhesive 66 is applied, the waist barrier 50 may be folded in half and attached to the absorbent article 10.

Figure 5:
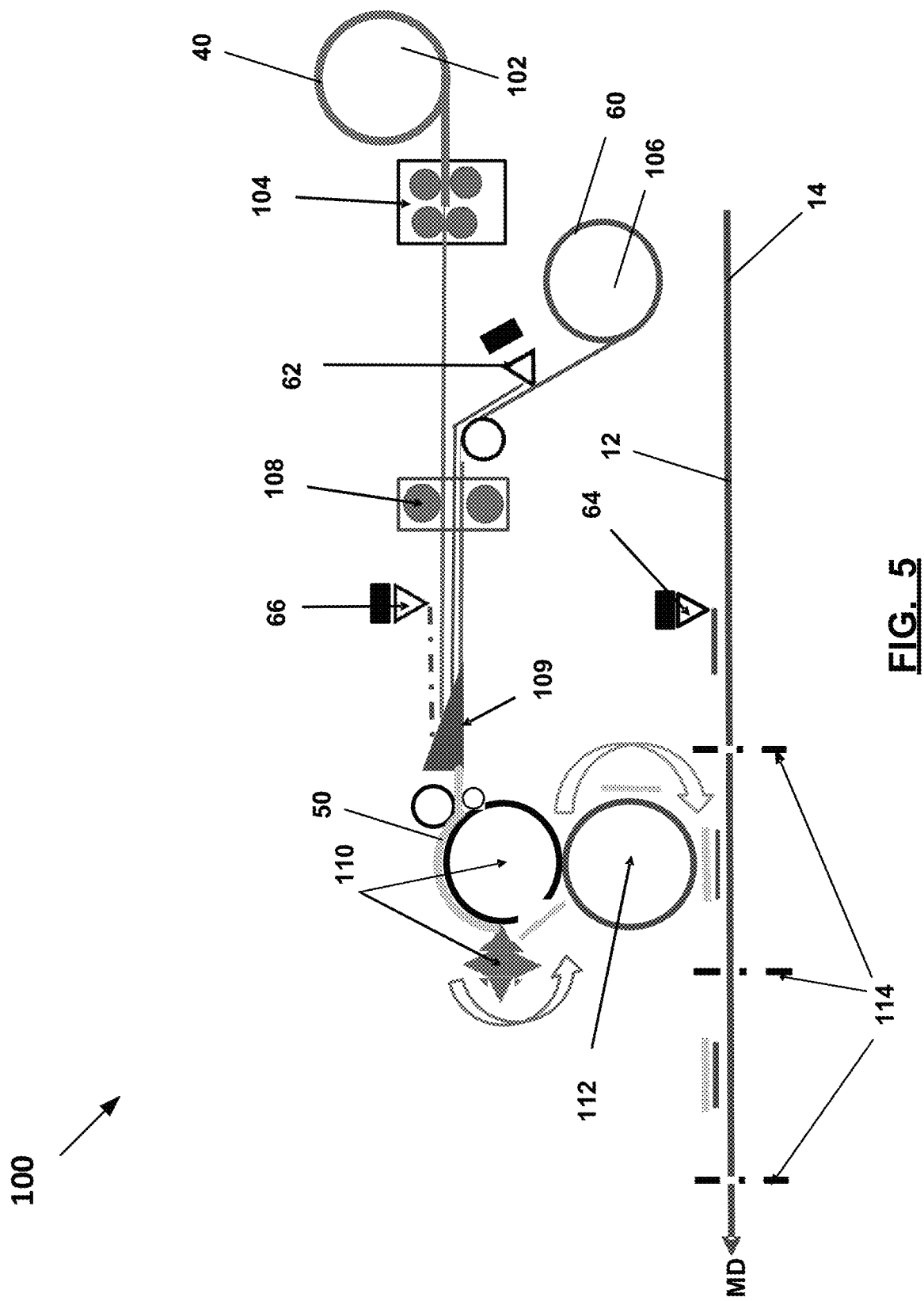
FIG. 5 shows a process schematic of a method to manufacture and attach the waist barrier to a disposable absorbent article in accordance with the previous example embodiment of FIG. 4A.

Referring to FIG. 5, shown therein is an exemplary embodiment of the process to manufacture the waist barrier 50 exemplified in FIG. 4A. The process begins by bonding the form material 52 to the nonwoven web 60 with the continuous adhesive pattern 62. Next, the intermittent adhesive pattern 66 may be phased and applied the form as shown in FIG. 4C. The phasing of the intermittent adhesive pattern 66 may be such that it is located at the longitudinal end regions 70, 74 of the waist barrier 50. Accordingly, the form 52 may be closed at each outer end region 70, 74 of the waist barrier 50 and open in the middle region 72, after being folded into a "c" configuration by folder 109. Next, a continuous adhesive pattern 64 may be applied to the underside of the bottom portion 53 of the waist barrier 50. Finally, the waist barrier 50 may be cut to size and placed on the inside of the absorbent article 10.

Still referring FIG. 5, a manufacturing machine 100 is exemplified, showing an exemplary method of fabricating and attaching the waist barrier 50 to an absorbent article 10. The easiest way to attach the waist barrier 50 to the absorbent article 10 on a manufacturing machine may be in the Machine Direction (MD). The product chassis of most training pant and protective underwear products, available in the marketplace today, may be manufactured in this direction. However, for diapers, the waist barrier 50 may be rotated 90 degrees and then attached to the absorbent article 10 (not shown).

First, the form 52 may be unwound from a roll, preferably from a traverse spool 102. The traverse spool 102 may improve the unwinding of a thick form material, as compared to the other thinner nonwoven materials used in the absorbent article 10. Traverse spools may allow more material to be wound on a roll and, thus, may allow longer run times on the high-speed manufacturing machines before splicing on a new roll. After the form 52 is unwound, it may optionally be stretched by a MD stretch station 104.

Next, adhesive 62 may be applied to one side of the nonwoven material 60 as it is unwound from second spool 106. Both materials are then compressed together with nip rolls 108. Then, adhesive 66 is applied in an intermittent pattern to the other side of the form 52. The form 52 is then folded in half, creating the waist barrier 50. The waist barrier 50 may then be cut on the "cut and place" unit 110, and accelerated on vacuum drum 112 to create spacing. Next, adhesive 64 may be applied to the topsheet 12, in an intermittent pattern, and phased to securely attach the waist barrier 50 to the inside of the article 10. The article 10 may then be cut to size with the cutter 114.

Figures 6A, 6B:
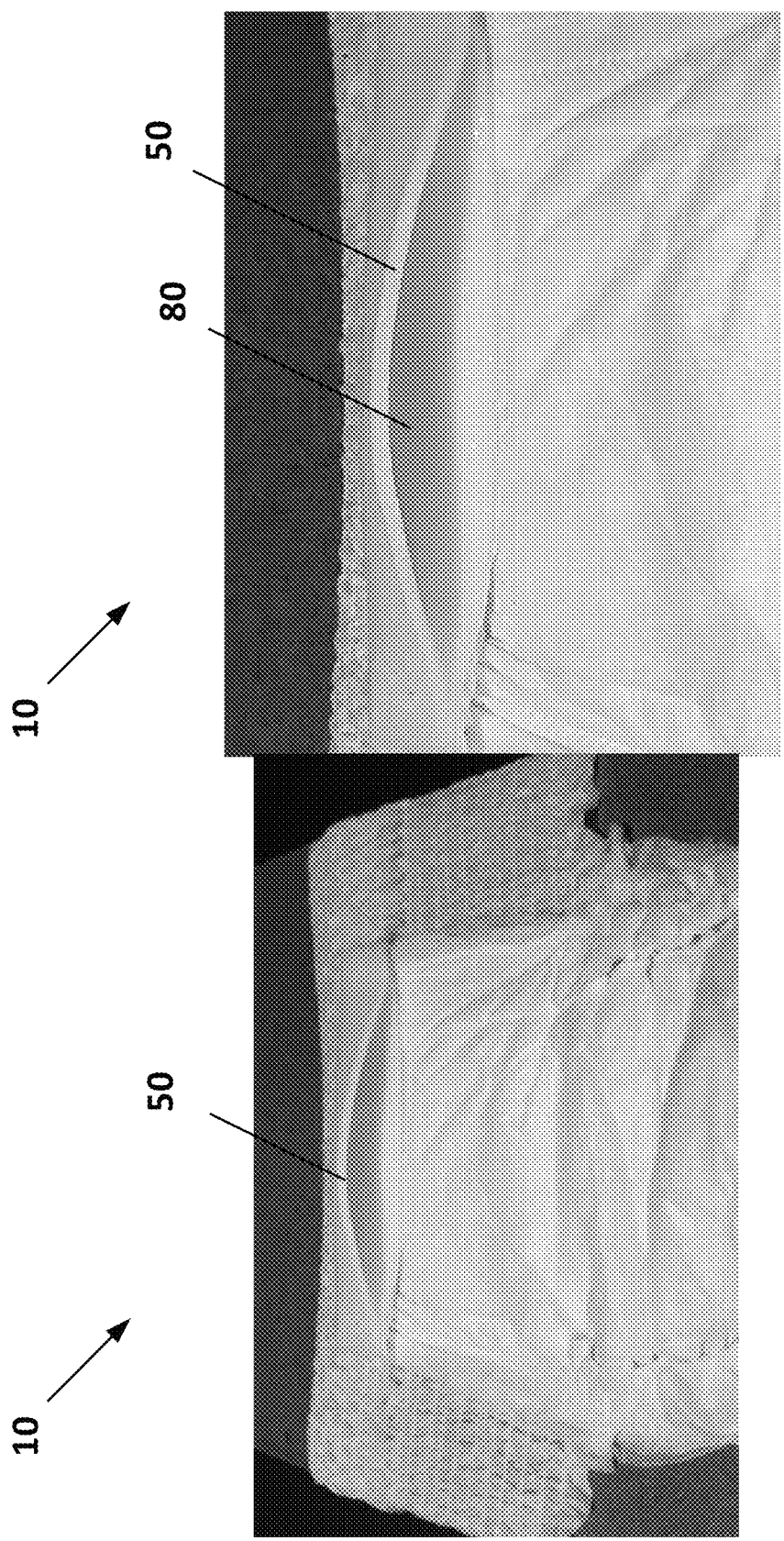
FIGS. 6A and 6B show images of the waist barrier applied to the rear waist area of an absorbent article, while in a latent state, in accordance with another example embodiment.
Figures 7A, 7B:
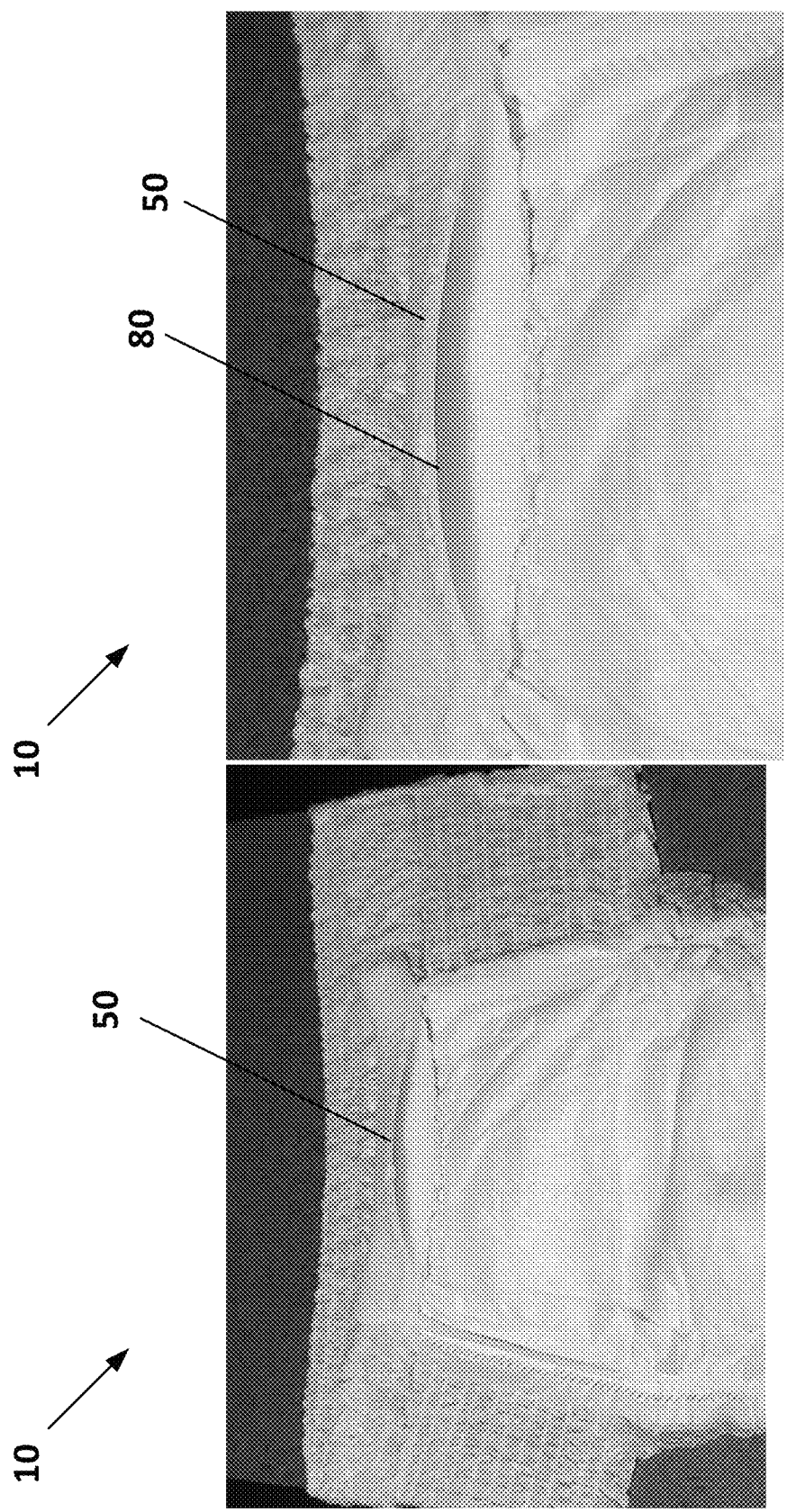
FIGS. 7A and 7B show images of the waist barrier applied to the rear waist area of the absorbent article of FIGS. 6A and 6B, while in the stretched state.

In some embodiments, the waist barrier 50 may be applied to the absorbent article 10 in the latent or unstretched state, as exemplified in FIGS. 6A and 6B. In some embodiments, the waist barrier 50 could be applied to the absorbent article 10 in a stretched or semi-stretched state, as exemplified in FIGS. 7A and 7B. FIGS. 6 and 7 illustrate how the form 52 pops-open in the middle region 72 to create an effective barrier against leakage along the waist area of the user.

Although the waist barrier 50 has mainly been described as being attached to absorbent articles 10, such as diapers and pants, it may be used for various other absorbent articles as well. These articles may include pads, shields, booster inserts, underpads, belted undergarments, pad and pant systems, disposable swimwear, etc. Typical pad products may include adult incontinence pads, feminine care pads, male guards, absorbent shields and other related articles. Illustrations of these type of products are not included.

One type of material that can be used for the form is a flexible polyurethane form available from Woodbridge Form located in Mississauga, Ontario, Canada.

One type of material that can be used as the resilient member 52 is a high loft nonwoven available from Shalag Nonwovens located in Oxford, North Carolina. These materials are typically hydrophobic carded webs that can be treated with surfactant to make it hydrophilic.

One type of material that can be used as the resilient member 52, which includes fluid-containing and sustainable fibers, is a nonwoven available from Spuntech Industries located in Roxboro, North Carolina, USA. The nonwoven contains both bamboo and viscose fibers, which are compostable.

One type of material that can be used as the resilient member 52, which contains thermoplastic and sustainable fibers, is a nonwoven available from Pelz-Tex GmbH & Co, located in Wahlstedt, Germany. The nonwoven contains 25% viscose, which is biodegradable. This material is stiffer than most nonwovens, which may provide increased resiliency.

One type of material that can be used for the nonwoven in the waist barrier 50 is a Spunbond Polypropylene (SBPP) or Spunbond-Meltblown-Spunbond (SMS) available from Berry Global located in Charlotte, North Carolina, USA.

One type of material that can be used for the standing leg cuffs 28a, 28b is a thin hydrophobic nonwoven, comprising of SMS (Spunbond-Meltblown-Spunbond), with a basis weight of 13.5 gsm, available from Berry Global located in Charlotte, North Carolina Other materials and basis weights can be used. This includes poly films, poly film & nonwoven laminates, extruded poly & nonwoven laminates, breathable films, breathable poly laminates, etc.

One type of material that can be used as the elastic strands 34 is a synthetic spandex thread identified as 800 dTex available from Hyosung located in Seoul, South Korea.

One type of material that can be used to adhere the elastic strands 34 to the standing leg cuffs 28a, 28b and waist barrier 50 is an elastic hot melt adhesive identified as H4356 available from Bostik Corporation located in Wauwatosa, WI.

One type of material that can be used to adhere the standing leg cuffs 28a, 28b to the topsheet 12 is a construction hot melt adhesive 36 identified as H4384 available from Bostik Corporation located in Wauwatosa, WI.

One type of absorbent core 20 that can be used is a mixture of cellulose pulp and super absorbent polymer that is wrapped in top nonwoven 24 and bottom nonwoven 26. One type of cellulose pulp that can be used is soft-pine ECF pulp available from Domtar located in Fort Mill, South Carolina One type of superabsorbent polymer that can be used is identified as Aquakeep HP650 available from Sumitomo Seika Chemicals Company located in Osaka, Japan. One type of nonwoven wrap that can be used is a 10 gsm hydrophilic nonwoven available from Berry Global located in Charlotte, North Carolina.

One type of material that can be used as the acquisition distribution layer 22 is hydrophilic high-loft nonwoven identified as ST6PERH50 from Shalag Nonwovens located in Oxford, North Carolina.

One type of material that can be used as the poly barrier 16 is a 0.65 mil polyethylene film available from Berry Global located in Charlotte, North Carolina.

Another type of material that can be used as the poly barrier 16 is a breathable poly laminate identified as XC3-121-2477 available from Berry Plastics located in Charlotte, North Carolina.

One type of material that can be used as the topsheet 12 is a 15 gsm zone-coated nonwoven available from Berry Global located in Charlotte, North Carolina.

One type of material that can be used as the backsheet 18 is 13.5 gsm soft hydrophobic nonwoven available from Fitesa located in Simpsonville, South Carolina.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims is not limited to the examples set out herein, but should be understood in a manner consistent with the description as a whole.

We claim:

1. An absorbent article having a front edge, a back edge, two longitudinally extending side edges, a front waist region, a rear waist region, a crotch region extending between the front waist region and the rear waist region, a skin-facing side, and a clothing-facing side, the absorbent article comprising:

a topsheet, the topsheet being liquid pervious;
a backsheet coupled to the topsheet, the backsheet being liquid impervious;
an absorbent core disposed between the topsheet and backsheet, the absorbent core containing at least one absorbent material;
an acquisition distribution layer disposed between a bottom side of the topsheet and a top side of the absorbent core;
first and second standing leg cuffs, each standing leg cuff includes:
  a base coupled to the topsheet; and
  one or more elastics coupled to a top of the standing leg cuff; and
a waist barrier located on the skin-facing side of one of the front waist region or the rear waist region, the waist barrier including:
  a top portion, a bottom portion, and a resilient member, the resilient member being folded to form the top portion and the bottom portion; and
  a first longitudinal end region, a second longitudinal end region, and a middle region between the first and second longitudinal end regions, the top portion and the bottom portion of the waist barrier being bonded together in the first and second longitudinal end regions, and the top portion of the waist barrier being unbonded to the bottom portion of the waist barrier in the middle region;
wherein the resilient member is inherently biased such that the resilient member is compressible towards the skin-facing side to form a biasing force in a direction away from the skin-facing side whereby a cavity is formed between the top portion and the bottom portion of the waist barrier in the unbonded middle region, and
wherein the resilient member has a length in a direction transverse to the longitudinal side edges that is at least a width of the crotch region.

2. The absorbent article of claim 1, further comprising a height between the topsheet and the top portion of the waist barrier on a cavity-facing side of the waist barrier, the waist barrier having an uncompressed state with a first height and a compressed state when worn by a user with a second height, wherein the first height is greater than the second height.

3. The absorbent article of claim 2, wherein the first height is at least twice a thickness of the waist barrier.

4. The absorbent article of claim 1, wherein the resilient member is at least partially covered by a cover sheet.

5. The absorbent article of claim 4, wherein the cover sheet is a hydrophobic nonwoven.

6. The absorbent article of claim 1, wherein at least one material of the waist barrier is fluid-containing.

7. The absorbent article of claim 1, wherein the waist barrier is at least partially absorbent.

8. The absorbent article of claim 1, wherein at least a portion of the waist barrier comprises one or more of bamboo, rayon, viscose, or cotton.

9. The absorbent article of claim 1, wherein the waist barrier is folded prior to being attached to the absorbent article.

10. The absorbent article of claim 1, wherein an underside of the bottom portion is bonded to the topsheet such that the top portion extends away from the bottom portion in the middle region of the waist barrier due to the bias of the resilient member.

11. The absorbent article of claim 1, further comprising a second waist barrier, wherein the waist barrier is a first waist barrier.

12. The absorbent article of claim 11, wherein the first waist barrier is located in the front waist region and the second waist barrier is located in the rear waist region.

13. The absorbent article of claim 1, wherein the waist barrier is attached to the absorbent article under tension.

14. The absorbent article of claim 1, wherein the waist barrier is attached to the absorbent article in a latent state.

15. The absorbent article of claim 1, wherein at least a portion of the topsheet and at least a portion of the waist barrier comprise different materials.

16. The absorbent article of claim 1, wherein at least one material of the waist barrier comprises a form.

17. The absorbent article of claim 1, wherein at least one material of the waist barrier comprises a high loft nonwoven.

18. The absorbent article of claim 1, wherein at least one material of the waist barrier comprises a hydrophobic nonwoven.

19. The absorbent article of claim 1, wherein the resilient member comprises a lofty nonwoven material.

* * * * *